United States Patent
Lee et al.

(10) Patent No.: US 10,404,784 B2
(45) Date of Patent: Sep. 3, 2019

(54) METHOD AND SYSTEM FOR TRANSMITTING RESULT OF EXAMINATION OF SPECIMEN FROM MEDICAL DEVICE TO DESTINATION

(71) Applicant: SAMSUNG ELECTRONICS CO., LTD., Suwon-si (KR)

(72) Inventors: Sung-hwa Lee, Anyang-si (KR); Se-do Gwon, Goyang-si (KR); Jong-rip Lee, Suwon-si (KR); Chang-sub Lee, Mokpo-si (KR); Sung-ho Choi, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 837 days.

(21) Appl. No.: 14/588,266

(22) Filed: Dec. 31, 2014

(65) Prior Publication Data
US 2015/0189001 A1 Jul. 2, 2015

Related U.S. Application Data

(63) Continuation-in-part of application No. 14/188,011, filed on Feb. 24, 2014.

(60) Provisional application No. 61/767,978, filed on Feb. 22, 2013.

(30) Foreign Application Priority Data

Jun. 25, 2013 (KR) ......................... 10-2013-0073314

(51) Int. Cl.
  *G16H 10/40* (2018.01)
  *H04L 29/08* (2006.01)
  (Continued)

(52) U.S. Cl.
  CPC .......... *H04L 67/10* (2013.01); *G06F 19/3418* (2013.01); *G06Q 10/0631* (2013.01);
  (Continued)

(58) Field of Classification Search
  CPC .... G06Q 50/22; G06Q 50/24; G06Q 10/0631; G06F 19/322; G06F 19/323–327;
  (Continued)

(56) References Cited

U.S. PATENT DOCUMENTS

6,269,276 B1 * 7/2001 Akhavan ................ G16H 10/40
  700/97
6,494,831 B1 12/2002 Koritzinsky
  (Continued)

FOREIGN PATENT DOCUMENTS

CN 1604533 A 4/2005
CN 1701335 A 11/2005
  (Continued)

OTHER PUBLICATIONS

Communication dated Jun. 21, 2016, issued by the State Intellectual Property Office of P.R. China in counterpart Chinese Application No. 201410062691.8.
  (Continued)

*Primary Examiner* — Jason S Tiedeman
(74) *Attorney, Agent, or Firm* — Sughrue Mion, PLLC

(57) ABSTRACT

Provided are a method and system for transmitting an examination result of a specimen from a medical device to a destination. The method of transmitting the examination result from the medical device to the destination includes: examining the specimen by using the medical device; receiving destination information indicating the destination to which the examination result will be transmitted, wherein the receiving is performed by the medical device; and transmitting the examination result to the destination corresponding to the destination information, wherein the transmitting is performed by the medical device.

24 Claims, 10 Drawing Sheets

(51) Int. Cl.
*H04W 8/18* (2009.01)
*G06Q 50/24* (2012.01)
*G06F 19/00* (2018.01)
*G06Q 10/06* (2012.01)

(52) U.S. Cl.
CPC ............. *G06Q 50/24* (2013.01); *G16H 10/40* (2018.01); *H04L 67/12* (2013.01); *H04W 8/18* (2013.01)

(58) Field of Classification Search
CPC .......... G06F 19/30; G06F 19/32; G06F 19/34; G06F 19/3418; G06F 19/36; G16H 10/00; G16H 10/60; G16H 15/00; G16H 40/00; G16H 40/40; G16H 40/60; G16H 40/63; G16H 40/67; G16H 50/00; G16H 50/20; G16H 50/80; G16H 80/00; G16H 10/40; H04L 67/10; H04L 67/12; H04W 8/18
USPC ........................................................ 705/2, 3
See application file for complete search history.

(56) References Cited

U.S. PATENT DOCUMENTS

| | | | |
|---|---|---|---|
| 6,699,195 B2 | 3/2004 | Nakazawa et al. | |
| 6,735,551 B2 | 5/2004 | Voegeli et al. | |
| 8,005,947 B2 | 8/2011 | Morris et al. | |
| 8,038,593 B2 | 10/2011 | Friedman et al. | |
| 8,111,817 B2 | 2/2012 | Hsu et al. | |
| 8,630,867 B2 | 1/2014 | Yoo | |
| 8,680,974 B2 | 3/2014 | Meiertoberens et al. | |
| 2002/0068858 A1* | 6/2002 | Braig | A61B 5/0002 600/316 |
| 2002/0169584 A1 | 11/2002 | Fu et al. | |
| 2003/0149598 A1 | 8/2003 | Santoso et al. | |
| 2003/0153297 A1 | 8/2003 | Falkiner et al. | |
| 2004/0057340 A1 | 3/2004 | Charles-Erickson et al. | |
| 2004/0059205 A1 | 3/2004 | Carlson et al. | |
| 2004/0077962 A1* | 4/2004 | Kroll | A61B 5/0452 600/513 |
| 2004/0199056 A1 | 10/2004 | Husemann et al. | |
| 2004/0204837 A1* | 10/2004 | Singleton | G01C 21/20 701/410 |
| 2005/0038326 A1 | 2/2005 | Mathur | |
| 2005/0102167 A1 | 5/2005 | Kapoor | |
| 2005/0192845 A1 | 9/2005 | Brinsfield et al. | |
| 2006/0036134 A1 | 2/2006 | Tarassenko et al. | |
| 2006/0062734 A1* | 3/2006 | Melker | G06F 19/3418 424/10.1 |
| 2006/0137699 A1* | 6/2006 | Moore | G06F 19/3418 705/2 |
| 2006/0284732 A1 | 12/2006 | Brock-Fisher | |
| 2007/0025877 A1* | 2/2007 | Hansen | A61B 5/7475 422/68.1 |
| 2007/0255114 A1 | 11/2007 | Ackermann et al. | |
| 2007/0270662 A1 | 11/2007 | Chen | |
| 2008/0021730 A1* | 1/2008 | Holla | G06F 19/3418 705/2 |
| 2008/0091175 A1 | 4/2008 | Frikart et al. | |
| 2008/0096495 A1 | 4/2008 | Shen | |
| 2008/0119705 A1* | 5/2008 | Patel | G06F 19/3418 600/347 |
| 2008/0140162 A1* | 6/2008 | Goetz | G06F 19/3418 607/60 |
| 2008/0242945 A1 | 10/2008 | Gugliotti et al. | |
| 2009/0063187 A1* | 3/2009 | Johnson | A61B 5/411 705/2 |
| 2009/0105567 A1 | 4/2009 | Smith et al. | |
| 2009/0240120 A1* | 9/2009 | Messinger | A61B 5/7445 600/301 |
| 2009/0273467 A1 | 11/2009 | Elixmann et al. | |
| 2010/0033332 A1 | 2/2010 | Heath et al. | |
| 2010/0081213 A1* | 4/2010 | Lee | B01L 3/502738 436/506 |
| 2010/0081895 A1 | 4/2010 | Zand | |
| 2010/0088393 A1* | 4/2010 | Udd | H04L 29/12462 709/217 |
| 2010/0094098 A1 | 4/2010 | Smith et al. | |
| 2010/0127885 A1* | 5/2010 | Okuno | G01N 33/48792 702/30 |
| 2010/0161003 A1 | 6/2010 | Malmberg et al. | |
| 2010/0274104 A1 | 10/2010 | Khan | |
| 2010/0295685 A1* | 11/2010 | Parvin | G06Q 50/22 340/573.1 |
| 2010/0298742 A1 | 11/2010 | Perlman et al. | |
| 2010/0309001 A1 | 12/2010 | Connolly et al. | |
| 2011/0015508 A1 | 1/2011 | Peyser | |
| 2011/0081888 A1* | 4/2011 | Waniss | H04M 1/72527 455/411 |
| 2012/0068847 A1 | 3/2012 | Pirzada | |
| 2012/0109688 A1 | 5/2012 | Yoo | |
| 2012/0143014 A1* | 6/2012 | Kim | G06F 19/3418 600/300 |
| 2012/0165639 A1* | 6/2012 | Engelhardt | G16H 40/40 600/365 |
| 2012/0167203 A1* | 6/2012 | Lee | G06F 19/00 726/19 |
| 2012/0184822 A1* | 7/2012 | Kim | A61B 5/00 600/300 |
| 2012/0197665 A1* | 8/2012 | Lewis | G06F 19/3481 705/3 |
| 2012/0309111 A1* | 12/2012 | Haustein | B01L 3/545 436/518 |
| 2012/0310660 A1 | 12/2012 | Liu et al. | |
| 2013/0078995 A1* | 3/2013 | Jouin | G06F 3/1438 455/426.1 |
| 2013/0096649 A1* | 4/2013 | Martin | G06F 19/3418 607/60 |
| 2013/0111353 A1* | 5/2013 | Ueda | G06Q 10/10 715/748 |
| 2013/0131994 A1* | 5/2013 | Birdwell | G06F 19/22 702/19 |
| 2013/0171678 A1* | 7/2013 | Karlsson | A61B 5/14546 435/26 |
| 2014/0096091 A1* | 4/2014 | Reid | G06F 19/3462 715/863 |
| 2014/0188498 A1* | 7/2014 | Petrimoulx | G06Q 30/0607 705/2 |

FOREIGN PATENT DOCUMENTS

| | | |
|---|---|---|
| CN | 1816794 A | 8/2006 |
| CN | 101252465 A | 8/2008 |
| CN | 101569521 A | 11/2009 |
| CN | 101620647 A | 1/2010 |
| CN | 101821722 A | 9/2010 |
| CN | 102356625 A | 2/2012 |
| EP | 0970655 A1 | 1/1998 |
| EP | 1107159 A2 | 11/2000 |
| EP | 1400259 B1 | 7/2005 |
| EP | 2315146 A1 | 1/2009 |
| EP | 2315146 A1 | 4/2011 |
| KR | 1020060124082 A | 12/2006 |
| KR | 10-0707098 B1 | 4/2007 |
| KR | 10-0783284 B1 | 12/2007 |
| KR | 1020100014065 A | 2/2010 |
| KR | 10-2010-0041660 A | 4/2010 |
| KR | 10-0975383 B1 | 8/2010 |
| WO | 2012060810 A1 | 5/2012 |

OTHER PUBLICATIONS

Tang et al: "Development and Application of Short Message Service Platform for Hospital" Chinese Medical Equipment Journal, vol. 30 No. 9, Sep. 30, 2009, pp. 46-48, (3 pages total).
Communication dated Feb. 24, 2017, issued by the State Intellectual Property Office of the People's Republic of China in counterpart Chinese Patent Application No. 201410062691.8.
Communication, dated Jul. 7, 2014 issued by the European Patent Office in counterpart Patent Application No. 14156204.1.

(56) References Cited

OTHER PUBLICATIONS

Communication, dated Jul. 7, 2014, issued by the European Patent Office in counterpart Patent Application No. 14156203.3.
Communication dated Sep. 28, 2014 issued by Korean Intellectual Property Office in counterpart Korean Application No. 10-2013-0073314.
Communication dated Aug. 16, 2017, issued by the State Intellectual Property Office of the People's Republic of China in counterpart Chinese Patent Application No. 201410062691.8.
Communication dated Oct. 26, 2017 by the State Intellectual Property Office of P.R. China in counterpart Chinese Patent Application No. 201410062465.X.
Communication dated Feb. 23, 2018, issued by the State Intellectual Property Office of the People's Republic of China in counterpart Chinese Patent Application No. 201410062691.8.
Communication dated Jun. 5, 2018, issued by the State Intellectual Property Office of the People's Republic of China in counterpart Chinese Patent Application No. 201410062465.X.
Communication dated Nov. 30, 2018, issued by the Chinese Patent Office in counterpart Chinese Application No. 201410062465.X.
Communication dated Jun. 13, 2016, issued by the Korean Intellectual Property Office in counterpart Korean Application No. 10-2013-0044881.
Communication dated Aug. 15, 2016, issued by the State Intellectual Property Office of P.R. China in counterpart Chinese Application No. 201410062465.X.

\* cited by examiner

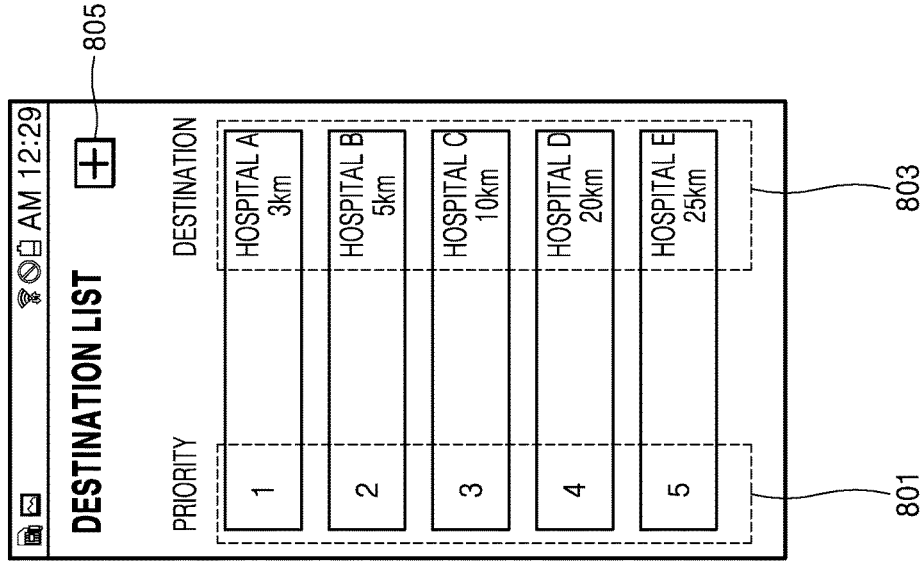

METHOD AND SYSTEM FOR TRANSMITTING RESULT OF EXAMINATION OF SPECIMEN FROM MEDICAL DEVICE TO DESTINATION

RELATED APPLICATIONS

This application is a Continuation-In-Part of U.S. patent application Ser. No. 14/188,011, filed on Feb. 24, 2014, which claims the benefit of U.S. Provisional Application No. 61/767,978, filed on Feb. 22, 2013, in the US Patent Office and Korean Patent Application No. 10-2013-0073314, filed on Jun. 25, 2013, in the Korean Intellectual Property Office, the disclosures of which are incorporated herein in their entireties by reference.

BACKGROUND

1. Field

One or more exemplary embodiments relate to a method and system for transmitting the result of examination of a specimen from a medical device to a destination.

2. Description of the Related Art

Ubiquitous healthcare (U-Health) integrates information technology (IT) with health and medical care to provide healthcare services such as prevention, diagnosis, treatment, and follow-up management of diseases. With dissemination of the U-Health concept, an increasing number of medical devices that are used inside or outside a hospital tend to be connected to one another via a network. However, when a medical device for providing examination and diagnosis functions is installed outside of a medical institution such as a hospital, i.e., is located within an ambulance, a retail clinic, etc., the medical device may have difficulty or a limitation in connecting with the medical institution through a network.

That is, the result of a medical examination that is provided by a medical device may be sent indirectly to medical staff through a telephone or printed material, or directly to a medical institution via a network. In the latter case, the examination results are transmitted only to a specified hospital. According to a conventional technique for transmitting results of medical examination from a medical device to a medical institution via a network, the medical device and a mobile phone within an ambulance are connected via Bluetooth so that the mobile phone receives the result of a medical examination from the medical device and simply conveys the same to a pre-specified medical institution. In other words, the mobile phone is only a medium through which the result of the medical examination is transmitted from the medical device to the pre-specified medical institution. Thus, if a patient is transported to a hospital other than the medical institution by the ambulance, the transmission of the examination results is useless.

Furthermore, since it is important that a medical device undergoes a quality control to ensure that the medical device maintains a predetermined level of quality, it is recommended for a user to periodically carry out a quality control test of the medical device. In an ambulance environment, the result of examination of a patient will be transmitted to a hospital to which the patient will be transported. However, the result of quality control testing of medical devices may be conveyed to a place other than the hospital, i.e., an organization responsible for management of the medical devices. For example, if a firehouse rescue center operates an ambulance, and a patient is transported to an unspecified number of hospitals, the result of quality control testing and the result of examination of the patient will have to be separately transmitted to different locations, respectively.

FIG. 1 is schematic diagram of a configuration in which a medical device 101 transmits the result of examination of a specimen to a destination, according to a conventional art.

If the medical device 101 examines a specimen to transmit the result of examination to a repeater 103, the repeater 103 then transmits the result of examination to a pre-specified hospital, i.e., hospital A. When the medical device 101 and the repeater 103 are installed in an ambulance outside a hospital, the medical device 101 transmits the result of examination to the repeater 103 via Bluetooth communication, which in turn transmits the result of examination to a pre-specified hospital via a wireless communication network. The repeater 103 generally takes the form of a mobile phone. In this case, if the patient is transported to a hospital other than the pre-specified one by an ambulance, the transmission of the examination results is useless.

SUMMARY

One or more exemplary embodiments include a method and system for effectively transmitting the result of examination of a specimen that is provided by a medical device.

One or more exemplary embodiments include a computer-readable recording medium having recorded thereon a program for executing the method on a computer.

One or more exemplary embodiments include a method and system for transmitting the result of examination to a destination corresponding to destination information received by a medical device.

One or more exemplary embodiments include a method and system for determining whether the result of examination that a medical device receives from a medical device is the result of examination of a patient's biological specimen or the result of quality control testing of the medical device. In this case, the result of examination of the patient's biological specimen and the result of quality control testing may be transmitted to different destinations, respectively.

Additional aspects will be set forth in part in the description which follows and, in part, will be apparent from the description, or may be learned by practice of the presented embodiments.

According to one or more exemplary embodiments, a method of transmitting an examination result of a specimen from a medical device to a destination includes: examining the specimen by using the medical device; receiving destination information indicating the destination to which the examination result will be transmitted, wherein the receiving is performed by the medical device; and transmitting the examination result to the destination corresponding to the destination information, wherein the transmitting is performed by the medical device.

The specimen may be a biological specimen extracted from an examinee.

In the transmitting of the examination result, information about the examinee's status may be transmitted together therewith.

The examination result may be the result of quality control testing that is conducted using quality control serum or an electronic quality control material for quality control of the medical device.

The medical device may determine whether the examination result is the result of examination of the examinee's biological specimen or the result of quality control testing of the medical device.

The destination may be at least one from among a server of a medical institution, a server of a medical information collection organization, and a mobile device held by an individual member of medical staff.

The server of the medical institution and the server of the medical information collection organization may be electronic medical record (EMR) servers.

The server of the medical institution and the server of the medical information collection organization may retransmit the examination result to the mobile device held by the individual member of medical staff.

The destination information may be received automatically from an emergency management server or input directly to the medical device.

A predetermined destination may be set as default destination information.

The predetermined destination may be at least one from among a medical device management server, a server of a medical institution, and a server of a medical information collection organization.

The destination information may include at least one from among a Uniform Resource Locator (URL), an Internet Protocol (IP) address, an Email address, and a telephone number of the destination.

The medical device and the destination may be connected to each other via at least one from among an Internet network, an Email network, a wireless communication network, a Short Message Service (SMS) network, and a Multimedia Messaging Service (MMS) network.

The result of the quality control testing of the medical device may be determined either automatically by the medical device for every predetermined period or manually by a user.

The result of quality control testing of the medical device may be determined either automatically by the medical device or by the destination.

When the medical device determines the result of quality control testing, the result of quality control testing may be indicated together on the result of examination of the examinee's biological specimen for transmission to the destination.

The medical device may include a wireless communication unit configured to transmit the examination result to the destination.

According to one or more exemplary embodiments, a wireless communication unit for transmitting an examination result of a specimen from a medical device to a destination includes a receiver for receiving destination information indicating the destination to which the examination result will be transmitted and a transmitter for transmitting the examination result to the destination corresponding to the destination information.

The specimen may be a biological specimen extracted from an examinee.

The examination result may be transmitted together with information about the examinee's status.

The specimen may be quality control serum or an electronic quality control material for quality control testing of the medical device.

The medical device may determine whether the examination result received from the medical device is the result of examination of the examinee's biological specimen or the result of quality control testing of the medical device.

The destination may be at least one from among a medical device management server, a server of a medical institution, and a server of a medical information collection organization The server of the medical institution and the server of the medical information collection organization may be EMR servers.

The server of the medical institution and the server of the medical information collection organization may retransmit the examination result to the mobile device held by the individual member of medical staff.

The destination information may be received automatically from an emergency management server or input directly to the medical device.

A predetermined destination may be set as default destination information.

The predetermined destination may be at least one from among a medical device management server, a server of a medical institution, and a server of a medical information collection organization.

The destination information may include at least one from among a URL, an IP address, an Email address, and a telephone number of the destination.

The medical device and the destination may be connected to each other via at least one from among an Internet network, an Email network, a wireless communication network, an SMS network, and an MMS network.

When the medical device determines the result of quality control testing, the result of quality control testing may be indicated together on the result of examination of the examinee's biological specimen for transmission to the destination.

According to one or more exemplary embodiments, a medical device for transmitting an examination result of a specimen to a destination includes: a specimen inserter for inserting the specimen; an examination and processing unit that examines the specimen and processes the examination result; and a wireless communication unit for transmitting the examination result to the destination, wherein the wireless communication unit includes a receiver for receiving destination information indicating the destination to which the examination result will be transmitted and a transmitter for transmitting the examination result to the destination corresponding to the destination information.

The specimen may be a biological specimen extracted from an examinee.

The examination result may be transmitted together with information about the examinee's status.

The specimen may be quality control serum or an electronic quality control material for quality control testing of the medical device.

The medical device may determine whether the examination result is the result of examination of the examinee's biological specimen or the result of quality control testing of the medical device.

The destination may be at least one from among a medical device management server, a server of a medical institution, and a server of a medical information collection organization.

The server of the medical institution and the server of the medical information collection organization may be EMR servers.

The server of the medical institution and the server of the medical information collection organization may retransmit the examination result to the mobile device held by the individual member of medical staff.

The destination information may be received automatically from an emergency management server or input directly to the medical device.

A predetermined destination may be set as default destination information.

The predetermined destination may be at least one from among a medical device management server, a server of a medical institution, and a server of a medical information collection organization.

The destination information may include at least one from among a URL, an IP address, an Email address, and a telephone number of the destination.

The medical device and the destination may be connected to each other via at least one from among an Internet network, an Email network, a wireless communication network, an SMS network, and an MMS network.

The result of the quality control testing of the medical device may be performed either automatically by the medical device for every predetermined period or manually by a user.

The result of quality control testing of the medical device may be determined either automatically by the medical device or by the destination.

When the medical device determines the result of quality control testing, the result of quality control testing may be indicated together on the result of examination of the examinee's biological specimen for transmission to the destination.

According to one or more exemplary embodiments, a non-transitory computer-readable recording medium has recorded thereon a program for executing the method on a computer.

As described above, since the result of examination of an examinee is transmitted from a medical device to an optimal destination, the examinee may not be transported to a pre-specified destination other than the optimal destination, thereby overcoming the problem of a conventional technique that transmission of the result of examination is useless. Furthermore, the result of examination of the examinee and the result of quality control testing of a medical device may be separately transmitted to different destinations, respectively, thereby allowing efficient management of medical devices.

In addition, the result of examination of a patient including the result of quality control testing of a medical device may be provided to medical staff, thereby preventing possible medical malpractice due to the medical staff relying on the wrong examination result.

BRIEF DESCRIPTION OF THE DRAWINGS

These and/or other aspects will become apparent and more readily appreciated from the following description of the embodiments, taken in conjunction with the accompanying drawings, and reference numerals therein denote structural elements, in which:

FIG. 7 is a schematic diagram of a screen of a medical device on which an application for transmitting the result of examination provided by a medical device is running, according to an exemplary embodiment;

FIG. 8 is a schematic diagram of a screen of a medical device on which an application for transmitting the result of examination provided by the medical device is running, according to another exemplary embodiment;

FIG. 11 is a schematic diagram of an exemplary screen for setting whether to transmit both the result of examination of an examinee (patient) and the result of quality control testing via an Email network selected from items shown in FIG. 10 when the result of examination is transmitted via the E-mail network;

FIG. 12 is a schematic diagram of an exemplary screen for setting whether to transmit both the result of examination of an examinee (patient) and the result of quality control testing via a Short Message Service (SMS) network selected from menu items shown in FIG. 10 when the result of examination is transmitted via the SMS network.

DETAILED DESCRIPTION

The terms used in this specification are general terms currently widely used in the art in consideration of functions in regard to the present invention, but the terms may vary according to the intention of one of ordinary skill in the art, precedents, or the occurrence of new technologies in the art. Also, specific terms may be selected by the applicant, and in this case, the detailed meaning thereof will be described in the detailed description of the invention. Thus, the terms used in the specification should be understood not as simple names but based on their meanings and the overall description of the invention.

Throughout the specification, it will also be understood that when a component "includes" an element, unless there is another opposite description thereto, the component does not exclude another element but may further include another element. In addition, terms such as " . . . unit", " . . . module", or the like refer to units that perform at least one function or operation, and the units may be implemented as hardware or software or as a combination of hardware and software. Expressions such as "at least one of," when preceding a list of elements, modify the entire list of elements and do not modify the individual elements of the list.

Exemplary embodiments will now be described more fully hereinafter with reference to the accompanying drawings.

Figure 1:
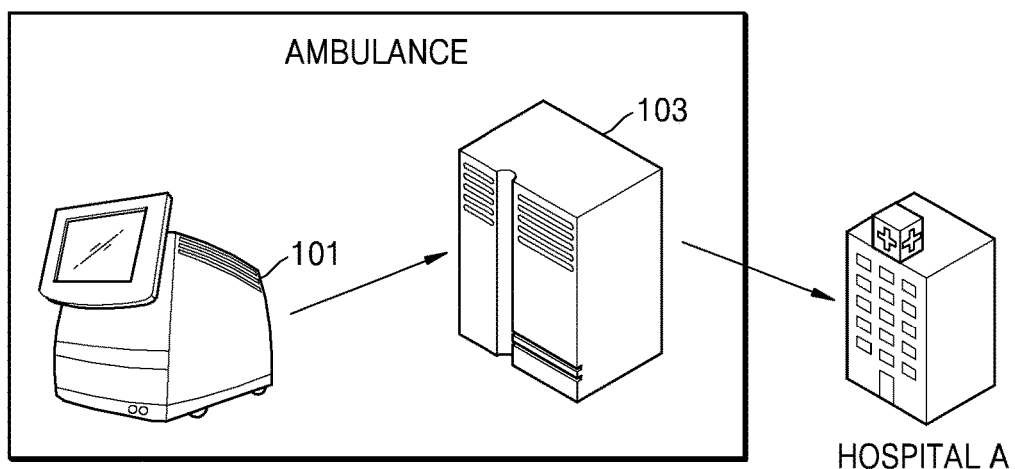
FIG. 1 is a schematic diagram of a configuration in which a medical device transmits the result of examination of a specimen to a destination, according to a conventional art.
Figure 2:
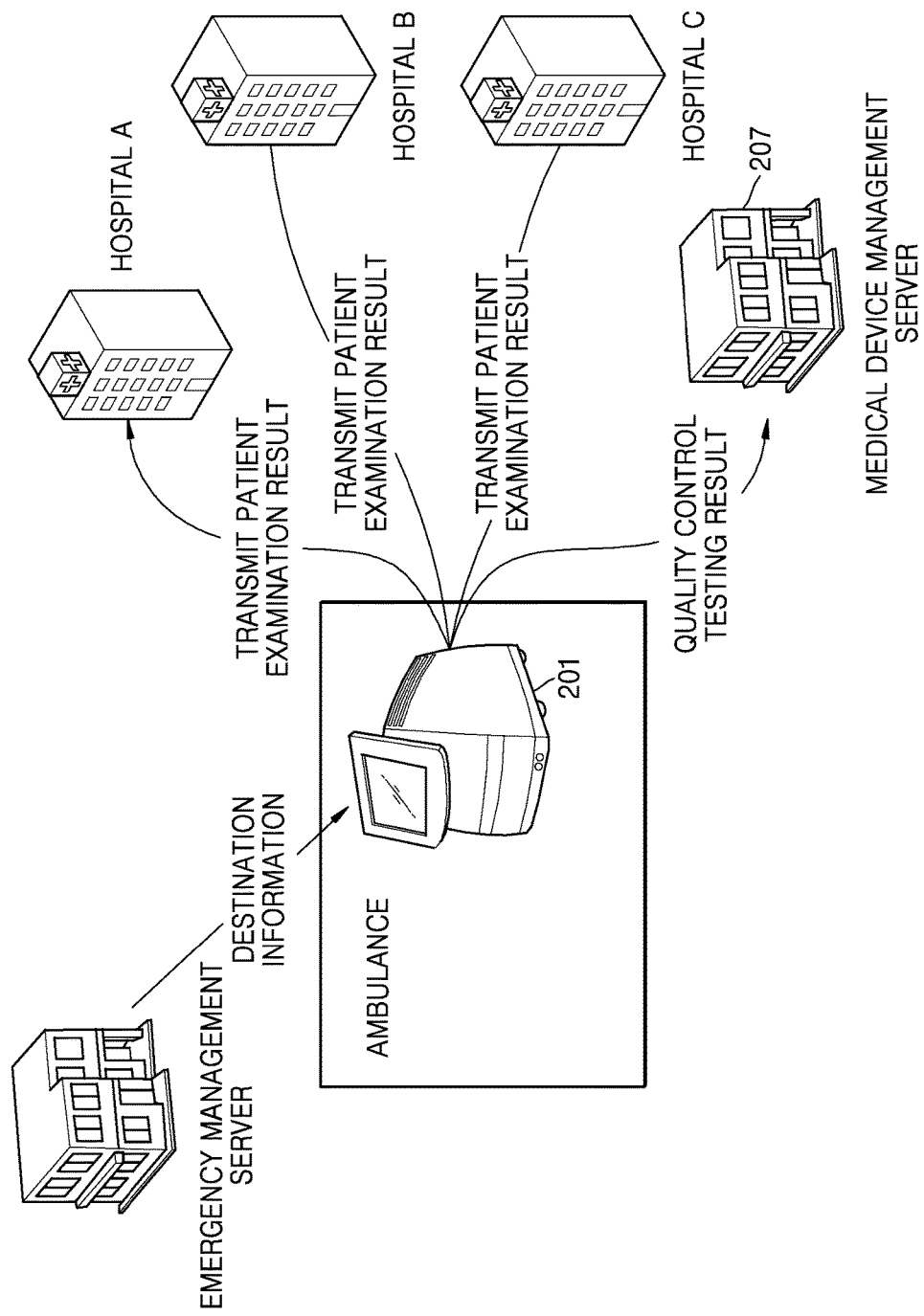
FIG. 2 is a schematic diagram of a system for transmitting the result of examination of a specimen from a medical device to a destination, according to an exemplary embodiment.
Figure 6:
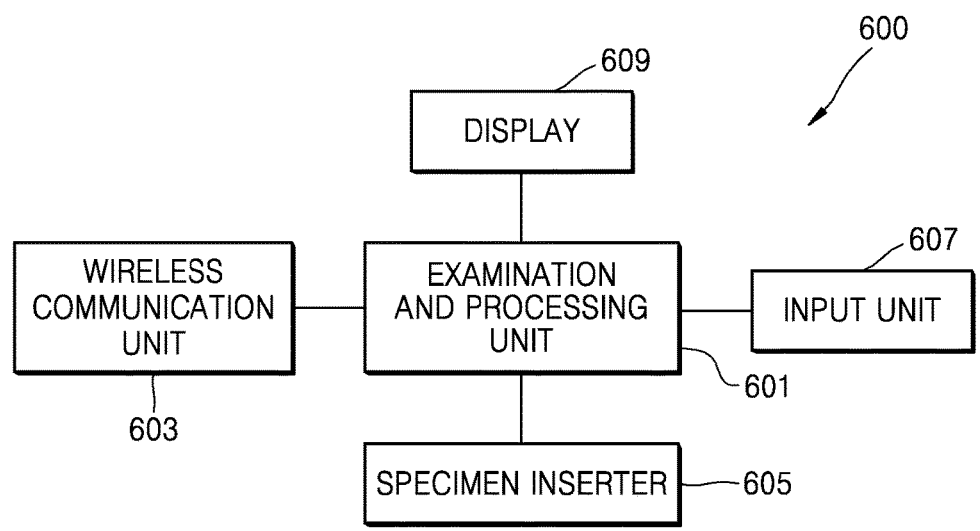
FIG. 6 is a schematic diagram of a medical device for transmitting the result of examination, according to an exemplary embodiment.

FIG. 2 is a schematic diagram of a system for transmitting the result of examination of a specimen from a medical device 201 to a destination, according to an exemplary embodiment. The medical device 201 is provided in the form of a terminal mounted in an ambulance. Although omitted hereinafter, the descriptions with respect to configurations shown in FIG. 6 are applied to the system of FIG. 2 as well.

After examining a specimen, the medical device 201 transmits the result of examination of the specimen to a destination. The medical device 201 may be connected to the destination via various wired or wireless networks such as Bluetooth and a wireless communication network. The networks are not limited to a specific network. The result of examination may be the result of examination of an examinee's biological specimen or the result of quality control testing of the medical device 201. If the result of examination is the result of examination of the examinee's biological specimen, the medical device 201 receives destination information indicating a destination to which the result of examination will be transmitted from an emergency management server 205 prior to transmitting the result of examination to the destination.

The medical device 201 may transmit the result of examination to a destination (at least one of hospitals A, B, and C) corresponding to the received destination information. The medical device 201 may be connected to the destination via various types of networks such as an Internet network, an Email network, a wireless communication network, a Short Message Service (SMS) network, a Multimedia Messaging Service (MMS) network, and other networks.

The destination information may be input directly to the medical device 201 by a user instead of being received from the emergency management server 205. In this case, the destination information may contain a Uniform Resource Locator (URL), an Internet Protocol (IP) address, an Email address, a telephone number of the destination, and other identifiers or addresses. The result of examination may be transmitted to the destination, along with information about the examinee' status. The information about the examinee's status is created by an emergency service worker who has observed the examinee's (patient's) status, and used together with the result of examination of the patient to help medical staff at the destination to identify the patient's status. Various biological samples such as blood may be used as a biological specimen extracted from the examinee. A specimen for use in quality control testing of the medical device 201 may be quality control serum or an electronic quality control material. The medical device 201 may identify whether the result of examination that is received from the medical device 201 is the result of examination of the examinee's biological specimen or the result of quality control testing of the medical device 201.

A destination to which the result of examination of the examinee's biological specimen will be transmitted may be a server of a medical institution, a server of a medical information collection organization, or a mobile device held by an individual member of the medical staff. The server of the medical institution or medical information collection organization may be an electronic medical record (EMR) server. Alternatively, the server of the medical institution or medical information collection organization may first receive the result of examination and then retransmit the same to a mobile device held by an individual member of medical staff. The result of examination of the examinee's biological specimen may be transmitted to only one destination (e.g., hospital A) or a plurality of destinations (e.g., hospitals A, B, and C). A destination to which the result of quality control testing of the medical device 201 will be transmitted may be a medical device management server 207, and information about the medical device management server 207 may be set as default destination information about the result of quality control testing. However, the present invention is not limited thereto, and the result of quality control testing may also be transmitted to a server of the medical institution or servers of the medical information collection organization. The quality control testing of the medical device 201 may be performed either automatically by the medical device 201 for every predetermined period or manually by a user. The result of quality control testing of the medical device 201 may be determined either automatically by the medical device 201 or by a destination such as the medical device management server 207. When the medical device 201 determines the result of quality control testing, the result of quality control testing may be indicated together on the result of examination of the examinee's biological specimen for transmission to a destination. A member of medical staff at the destination may assess the reliability of the result of the examinee's biological specimen by referring to the result of quality control testing added thereto.

Figure 3:
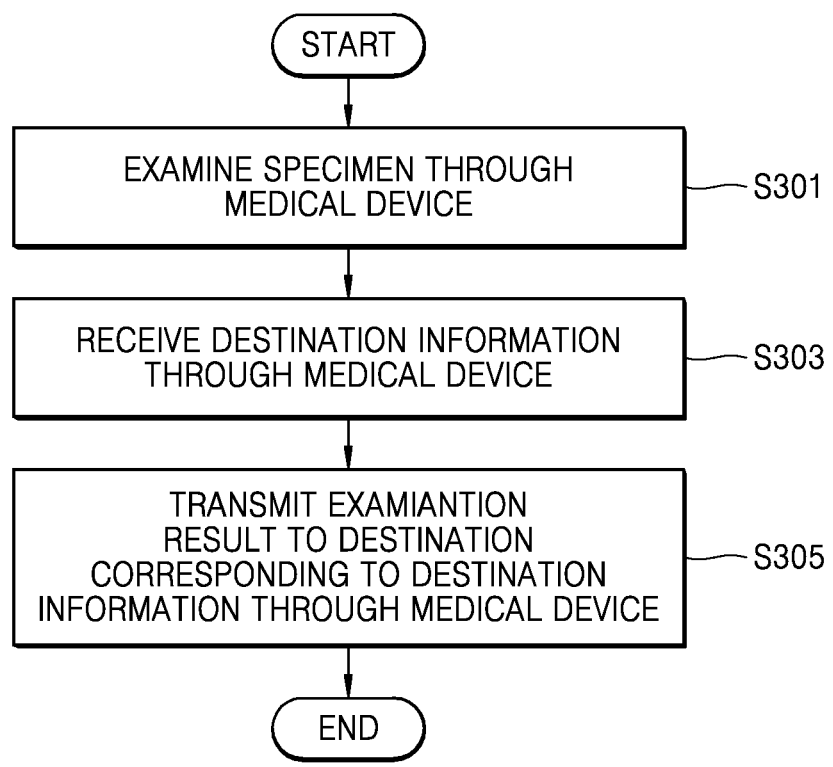
FIG. 3 is a flowchart of a method of transmitting the result of examination from a medical device to a destination, according to an exemplary embodiment.

FIG. 3 is a flowchart of a method of transmitting the result of examination from a medical device to a destination, according to an exemplary embodiment. The method according to the present embodiment includes operations performed by a medical device 700 of FIG. 6 in a time series. Thus, although omitted hereinafter, the descriptions with respect to configurations shown in FIG. 6 may also be applied to the method of FIG. 3.

Referring to FIG. 3, the medical device examines a sample to be inspected (hereinafter, referred to as a 'specimen') (S301). The specimen may generally include various biological tissues that are extracted from an examinee's body. A representative specimen may be the examinee's blood, but is not limited thereto. The specimen may be any specimen other than biological tissue extracted from the examinee as long as it can be inspected by the medical device. A specimen for use in quality control testing of the medical device may be quality control serum or electronic quality control material.

The result of examination may be the result of examination of an examinee's biological specimen or the result of quality control testing of the medical device. The medical device may determine whether the result of examination is the result of examination of the examinee's biological specimen or the result of quality control testing of the medical device.

The medical device receives destination information indicating a destination to which the result of examination will be transmitted (S303). If the result of examination is the result of examination of the examinee's biological specimen, the medical device receives destination information indicating a destination to which the result of examination will be transmitted from an emergency management server before transmitting the result of examination to the destination. The destination information may be input directly to the medical device by the user instead of being received from the emergency management server. In this case, the destination information may contain a URL, an IP address, an Email address, and a telephone number of the destination.

The medical device transmits the result of examination to the destination corresponding to the destination information (S305). A destination to which the result of examination of the examinee's biological specimen is transmitted may be a server of a medical institution, a server of a medical information collection organization, or a mobile device held by an individual member of medical staff. The server of the medical institution or medical information collection organization may be an EMR server. Alternatively, the server of the medical institution or medical information collection organization may first receive the result of examination and then retransmit the same to a mobile device held by an individual member of medical staff. The result of examination of the examinee's biological specimen may be transmitted to only one destination (e.g., hospital A) or a plurality of destinations (e.g., hospitals A, B, and C). A destination to which the result of quality control testing of the medical device will be transmitted may be a medical device management server, and the medical device management server may be set as default destination information about the result of quality control testing. However, the present invention is not limited thereto, and the result of quality control testing may also be transmitted to a server of the medical institution or servers of the medical information collection organization. Furthermore, the user may directly input destination information about the result of quality control testing. The medical device may be connected to the destination via various types of networks such as an Internet network, an Email network, a wireless communication network, an SMS network, and an MMS network.

The result of quality control testing of the medical device may be determined either automatically by the medical device or by a destination such as the medical device management server. If the medical device determines the result of quality control testing, the result of quality control testing may be indicated together on the result of examination of the examinee's biological specimen for transmission to a destination. Furthermore, the result of examination may be transmitted to the destination with information about the examinee' status added thereto. The information about the examinee's status is created by an emergency service worker who has observed the examinee's (patient's) status, and used together with the result of examination of the patient to help medical staff at the destination to identify the patient's status.

Figure 4:
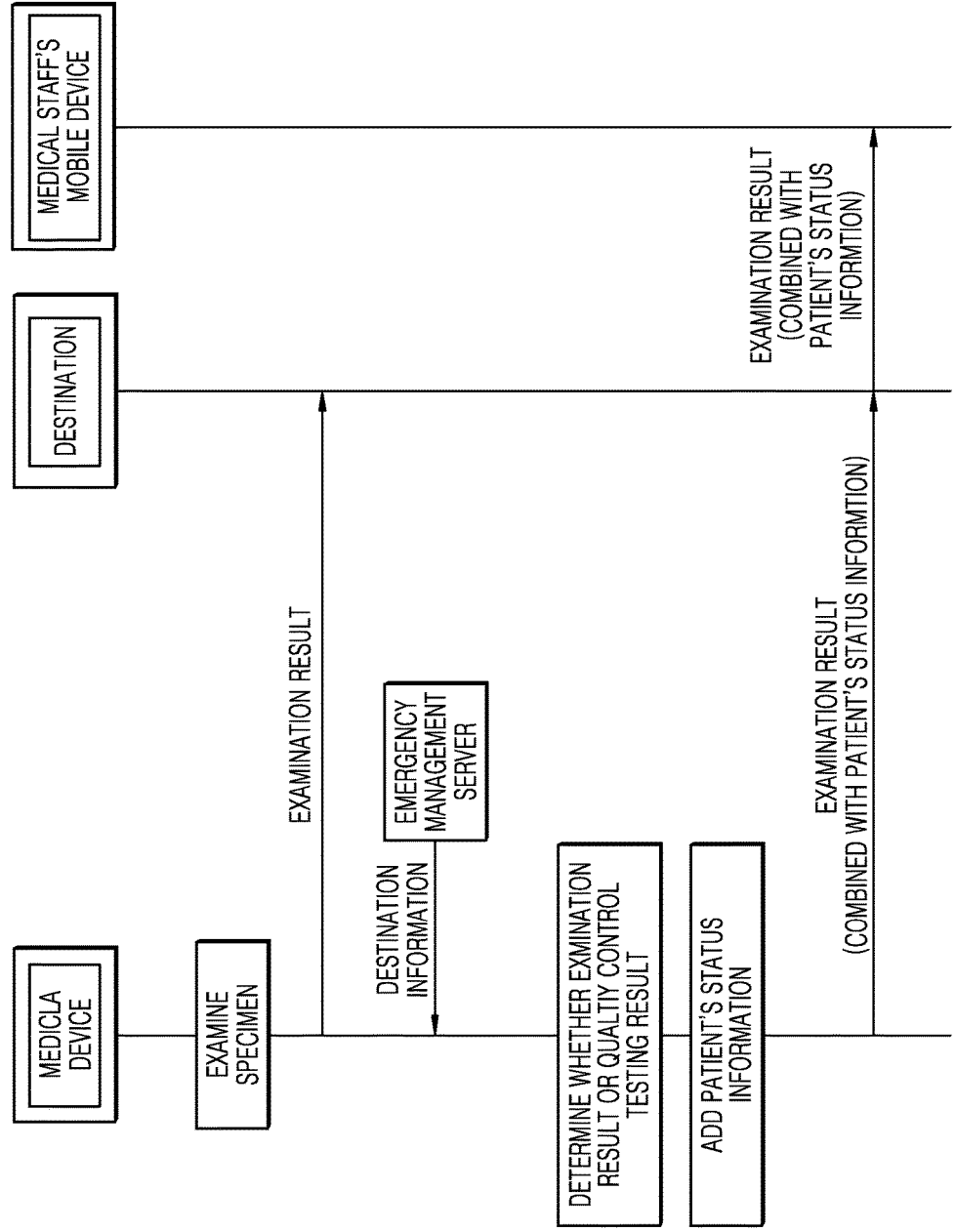
FIG. 4 is a schematic diagram of a system for transmitting the result of examination of a specimen from a medical device to a destination t, according to an exemplary embodiment.

FIG. 4 is a schematic diagram of a system for transmitting the result of examination of a specimen from a medical device to a destination, according to an exemplary embodiment. Operations of the system of FIG. 4 include operations performed by the medical device 600 of FIG. 6 in a time series. Thus, although omitted hereinafter, the descriptions with respect to configurations shown in FIG. 6 may also be applied to the system of FIG. 4.

The medical device examines a specimen. The specimen may generally include various biological tissues that are extracted from an examinee's body. A representative specimen may be the examinee's blood, but is not limited thereto. The specimen may be any specimen other than biological tissue extracted from the examinee, which can be inspected by the medical device. A specimen for use in quality control testing of the medical device may be quality control serum or electronic quality control material. The quality control testing of the medical device may be performed either automatically by the medical device for every predetermined period or manually by a user.

The medical device may determine whether the result of examination is the result of examination of the examinee's biological specimen or the result of quality control testing of the medical device.

The medical device receives destination information indicating a destination to which the result of examination will be transmitted. If the result of examination is the result of examination of the examinee's biological specimen, the medical device receives destination information indicating a destination to which the result of examination will be transmitted from an emergency management server before transmitting the result of examination to the destination. The destination information may be input directly to the medical device by the user instead of being received from the emergency management server. In this case, the destination information may contain a URL, an IP address, an Email address, and a telephone number of the destination.

The medical device transmits the result of examination to a destination corresponding to destination information. The result of examination may be transmitted to the destination with information about the examinee' status added thereto. The information about the examinee's status is created by an emergency service worker who has observed the examinee's (patient's) status, and used together with the result of examination of the patient to help medical staff at the destination to identify the patient's status. A destination to which the result of examination of the examinee's biological specimen is transmitted may be a server of a medical institution, a server of a medical information collection organization, or a mobile device held by an individual member of medical staff. The server of the medical institution or medical information collection organization may be an EMR server. Alternatively, the server of the medical institution or medical information collection organization may first receive the result of examination and then retransmit the same to a mobile device held by an individual member of medical staff. The result of examination of the examinee's biological specimen may be transmitted to only one destination (e.g., hospital A) or a plurality of destinations (e.g., hospitals A, B, and C). The medical device may be connected to the destination via various types of networks such as an Internet network, an Email network, a wireless communication network, an SMS network, and an MMS network.

Figure 5:
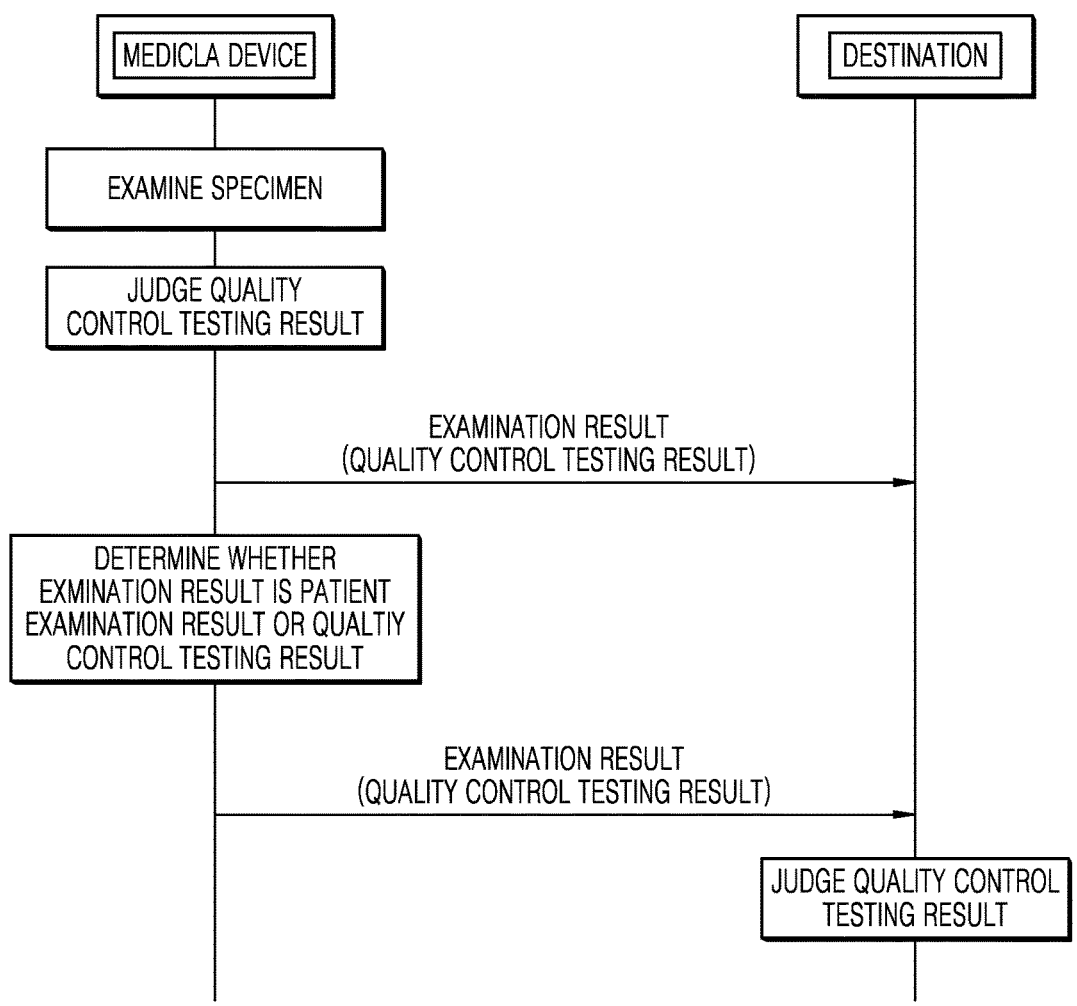
FIG. 5 is a schematic diagram of a system for transmitting the result of quality control testing of a medical device, according to an exemplary embodiment.

FIG. 5 is a schematic diagram of a system for transmitting the result of quality control testing of a medical device, according to an exemplary embodiment. Operations of the system of FIG. 5 include operations performed by the medical device 600 of FIG. 6 in a time series. Thus, although omitted hereinafter, the descriptions with respect to configurations shown in FIG. 6 may be applied to the system of FIG. 5 as well.

The medical device examines a specimen. A specimen for use in quality control testing of the medical device may be quality control serum or electronic quality control material. The quality control testing of the medical device may be performed either automatically by the medical device for every predetermined period or manually by a user.

The medical device may determine whether the result of examination is the result of examination of an examinee's biological specimen or the result of quality control testing of the medical device.

The medical device transmits the result of quality control testing to a destination corresponding to destination information. A destination to which the result of quality control testing of the medical device will be transmitted may be a medical device management server, and the medical device management server may be set as default destination information about the result of quality control testing. However, the present invention is not limited thereto, and the result of quality control testing may also be transmitted to a server of a medical institution or servers of a medical information collection organization. Furthermore, the user may directly input destination information about the result of quality control testing. The medical device may be connected to the destination via various types of networks such as an Internet network, an Email network, a wireless communication network, an SMS network, and an MMS network. The result of quality control testing of the medical device may be determined either automatically by the medical device or by a destination such as the medical device management server. If the medical device determines the result of quality control testing, the result of quality control testing may be indicated together on the result of examination of the examinee for transmission to a destination.

FIG. 6 is a schematic diagram of a medical device 600 for transmitting the result of examination to a destination, according to an exemplary embodiment. Referring to FIG. 6, the medical device 600 according to the present embodiment includes an examination and processing unit 601, a wireless communication unit 603, a specimen inserter 605, an input unit 607, and a display 609.

The specimen inserter 605 is configured to insert a specimen to be inspected. The specimen may generally include various biological tissues that are extracted from an examinee's body. A representative specimen may be the examinee's blood, but is not limited thereto. The specimen may be any specimen other than biological tissue extracted from the examinee as long as it can be inspected by the medical device 600. A specimen for use in quality control testing of the medical device 600 may be quality control serum or electronic quality control material. The quality control testing of the medical device 600 may be performed either automatically by the medical device 600 for every predetermined period or manually by a user.

The examination and processing unit 601 performs examination of a specimen in the same manner that medical examination equipment generally performs and processes the result of examination. The result of examination means details of the examination including examination items, examination result values, completion/incompletion of the examination, occurrence of abnormalities, falling in a critical range, the result of quality control testing, etc., and is symmetrically arranged and processed.

The examination and processing unit 601 also determines whether the result of examination is the result of examination of the examinee's biological specimen or the result of quality control testing of the medical device 600.

The wireless communication unit 603 receives the result of examination of the specimen and destination information indicating a destination to which the result of examination will be transmitted. The medical device 600 and the destination may be connected via various wired or wireless networks such as Bluetooth and wired or wireless communication networks. The networks are not limited to a particular network. The result of examination that is transmitted to the destination is the result of examination of the examinee's biological specimen or the result of quality control testing of the medical device 600. If the result of examination is the result of examination of the examinee's biological specimen, the medical device 600 receives destination information indicating a destination to which the result of examination will be transmitted from an emergency management server before transmitting the result of examination to the destination. The destination information may be input directly to the medical device 600 by the user via the input unit 607 instead of being received from the emergency management server. In this case, the destination information may contain a Uniform Resource Locator (URL), an Internet Protocol (IP) address, an Email address, and a telephone number of the destination.

The wireless communication unit 603 also transmits the result of examination to a destination corresponding to destination information. A destination to which the result of examination of the examinee's biological specimen will be transmitted may be a server of a medical institution, a server of a medical information collection organization, a mobile device held by an individual member of medical staff, etc. The server of the medical institution or the server of the medical information collection organization may be an electronic medical record (EMR) server. The server of the medical institution or the server of the medical information collection organization may first receive the result of examination and then retransmit the same to a mobile device held by an individual member of medical staff. The result of examination of the examinee's biological specimen may be transmitted to only one destination (e.g., hospital A) or a plurality of destinations (e.g., hospitals A, B, and C). A destination to which the result of quality control testing of the medical device 600 will be transmitted may be a medical device management server, and information about the medical device management server may be set as default destination information about the result of quality control testing. However, exemplary embodiments are not limited thereto, and the result of quality control testing may also be transmitted to a server of the medical institution or servers of the medical information collection organization. Destination information about the result of quality control testing may also be input directly by a user. The mobile medical device 600 may be connected to the destination via various types of networks such as an Internet network, an Email network, a wireless communication network, an SMS network, an MMS network, and other networks. The result of quality control testing of the medical device 600 may be determined either automatically by the medical device 600 or by a destination such as a medical device management server. When the medical device 600 determines the result of quality control testing, the result of quality control testing may be indicated together on the result of examination of the examinee's biological specimen for transmission to a destination. The result of examination may be transmitted to the destination with information about the examinee' status added thereto. The information about the examinee's status is created by an emergency service worker who has observed the examinee's (patient's) status, and used together with the result of examination of the examinee to help medical staff at the destination to identify the patient's status.

FIG. 7 is a schematic diagram of a screen of a medical device on which an application for transmitting the result of examination provided by a medical device runs, according to an exemplary embodiment.

The medical device receives destination information indicating a destination to which the result of examination provided by the medical device will be transmitted from an emergency management server. The destination information may be one or a plurality of pieces of destination information corresponding to one or a plurality of destinations. As shown in FIG. 7, destinations corresponding to the destination information may be displayed on the screen as a list. Brief information 803 about each destination such as a name of a medical institution (hospital) and a distance between the destination and the current location may also be displayed together in the list. Furthermore, priorities 801 for the destinations may be determined by an emergency management server in consideration of a distance between each destination and the current location or the characteristics of the medical institution (general hospital/clinic and provision of an emergency room) and be displayed in the list together with the destinations. In this case, the result of examination may be automatically transmitted to a medical institution (hospital A) having the highest priority, or to several medical institutions having high priorities such as two or three destinations, e.g., hospitals A, B, and C. A particular button 805 may allow the user to manually enter a destination, as described below with reference to FIG. 8.

FIG. 8 is a schematic diagram of a screen of medical device on which an application for transmitting the result of examination provided by a medical device runs, according to another exemplary embodiment.

Figure 9:
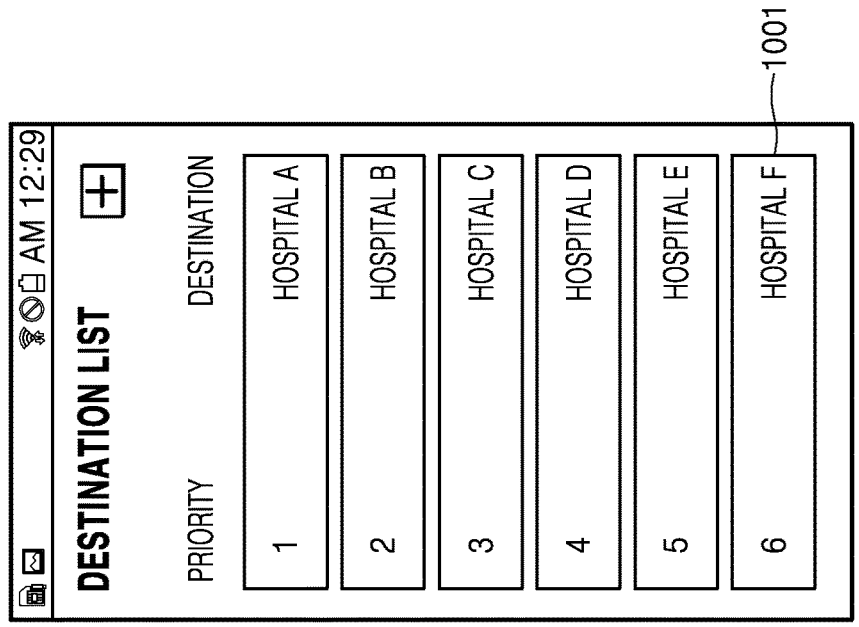
FIG. 9 is a schematic diagram of an exemplary screen that displays a destination (hospital F) added to a destination list shown in FIG. 7 after pressing a button 'Complete Input' on the screen shown in FIG. 8.
Figure 10:
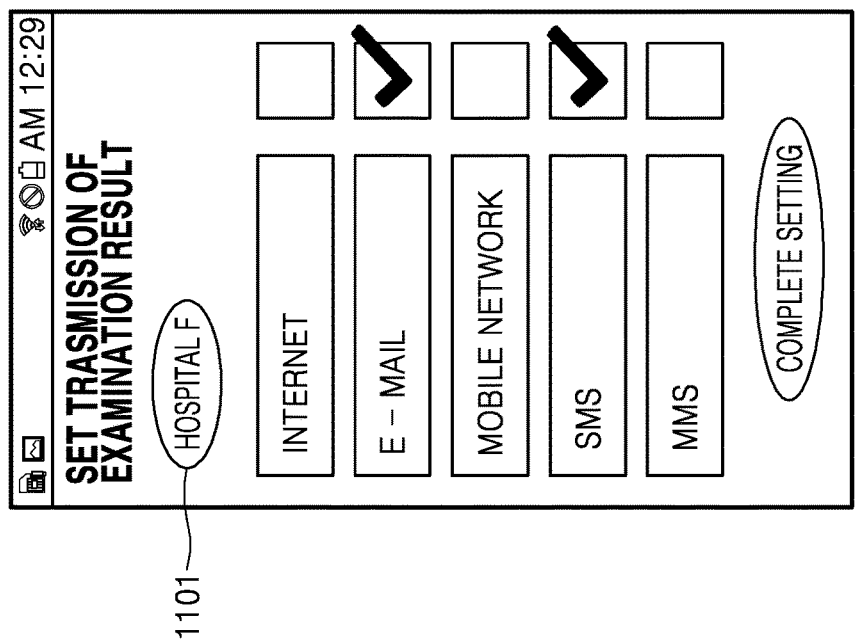
FIG. 10 is a schematic diagram of a transmission setting screen that appears after pressing a button 'Set Transmission' on the screen shown in FIG. 8.
Figures 11, 12:
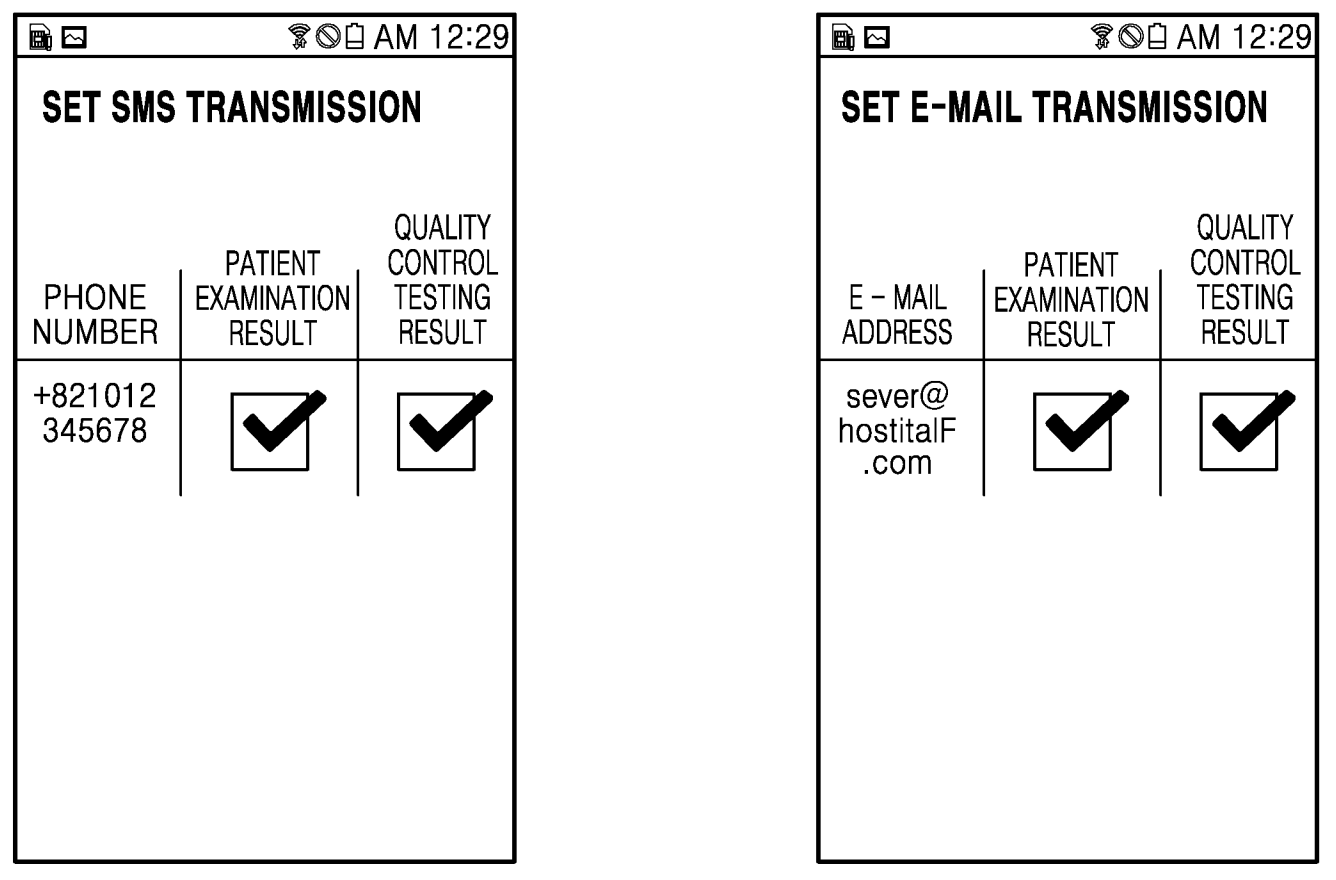

When the particular button 805 is pressed on the screen of FIG. 7, a screen that allows a user to manually input a destination is displayed. The user may enter destination information such as a name, a telephone number, an address, a URL, an IP address, and an E-mail address of the destination. When the user presses a button 'Complete Input' after entering the destination information, a new input destination (hospital F) is added to the list as shown in FIG. 9. By pressing a button 'Transmit Examination Result' on the screen of FIG. 8, the result of examination may be transmitted directly to the input destination. Furthermore, when a button 'Set Transmission' is pressed on the screen of FIG. 8, a transmission setting screen for the hospital F appears as shown in FIG. 10. The medical device may be connected to a destination via an Internet network, an Email network, a wireless communication network, an SMS network, an MMS network, or the like, and select a network to be used for transmission of the result of examination from among these networks. FIG. 10 shows setting of transmission of the examination result via an Email network and an SMS network. Referring to FIG. 10, a check box next to each item representing a network may be checked to set transmission of the examination result via the network for the item. If the examination result is transmitted via the Email network, it is possible to set whether to transmit both the result of examination of an examinee (patient) and the result of quality control testing via the Email network. Referring to FIG. 11, a check box for an item representing the result of examination of a patient or the result of quality control testing may be checked to set transmission of the result of examination corresponding to the item. Thus, if a user enters destination information directly to the medical device, at least one of the result of examination of an examinee and the result of quality control testing may be set to be transmitted to a destination corresponding to the destination information. Similarly, if the result of examination is transmitted via an SMS network, it is possible to set whether to transmit both the result of examination of an examinee (patient) and the result of quality control testing via the SMS network. Referring to FIG. 12, a check box for an item representing the result of examination of a patient or the result of quality control testing may be checked to set transmission of the result of examination corresponding to the item. If a user enters destination information directly to the medical device, at least one of the result of examination of an examinee and the result of quality control testing may be set to be transmitted to a destination corresponding to the destination information.

Figure 13A:
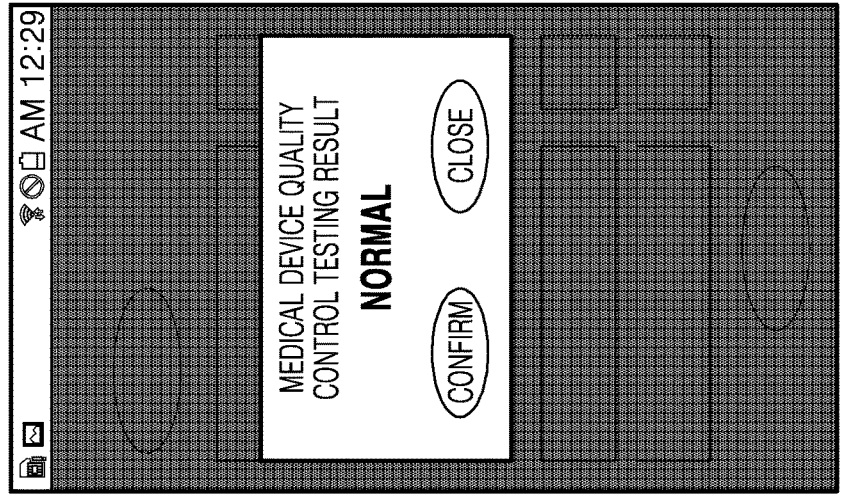
FIGS. 13A, and 13B are schematic diagrams of an exemplary screen of a display of a medical device on which the result of quality control testing of a medical device is displayed in a popup window.
Figure 13B:
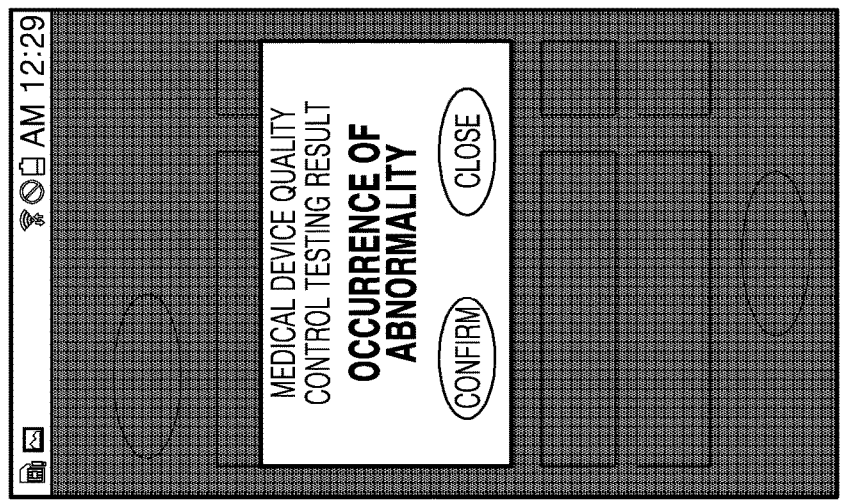

The result of quality control testing of the medical device may be determined either automatically by a medical device or by a destination such as a medical device management server. If the medical device determines the result of quality control testing, the result of quality control testing may be indicated together on the result of examination of the examinee for transmission to a destination. Referring to FIGS. 13A and 13B, the result of quality control testing of the medical device may be displayed on a display screen of the mobile device in a popup window.

The above methods according to the embodiments of the present invention can be recorded as programs that can be executed on a computer and be implemented through general-purpose digital computers which can run the programs using a computer-readable recording medium. Data structures described in the above method can also be recorded on a computer-readable recording medium in a variety of ways. Program storage devices that can be used to describe a storage device containing computer codes executable to perform various methods according to the present invention are not understood to include transitory media such as carrier waves or signals. Examples of the computer-readable recording medium include recording media, such as magnetic storage media (e.g., ROM, floppy disks, hard disks, etc.), and optical recording media (e.g., CD-ROMs or DVDs).

While one or more embodiments of the present invention have been described with reference to the figures, it will be understood by one of ordinary skill in the art that various changes in form and details may be made therein without departing from the spirit and scope of the present invention as defined by the following claims. Thus, it should be understood that the exemplary embodiments described therein should be considered in a descriptive sense only and not for purposes of limitation. The scope of the invention is defined not by the detailed description of the invention but by the appended claims, and all differences within the scope of the appended claims and their equivalents will be construed as being included in the present invention.

What is claimed is:

1. A method of transmitting an examination result of a specimen, from a medical device to a destination, the method comprising:

examining the specimen, using the medical device;

receiving, by the medical device, destination information indicating two or more destinations to which the examination result is to be transmitted;

displaying, by the medical device, the destination information together with priority information for each of the two or more destinations;

determining, by the medical device, at least one destination from among the two or more destinations;

displaying, by the medical device, a transmission setting screen for the determined at least one destination, wherein the transmission setting screen indicates networks usable to transmit the examination result to the determined at least one destination;

receiving, by the medical device, a selection of at least one of the networks indicated by the displayed transmission setting screen;

receiving, by the medical device, a selection of at least one from among a first item representing the examination result of the specimen and a second item representing a result of quality control testing of the medical device;

transmitting, by the medical device, the examination result of the specimen, to the determined at least one destination, via the selected at least one of the networks, in response to the selection of the first item being received; and transmitting, by the medical device, the result of quality control testing of the medical device, to the determined at least one destination, via the selected at least one of the networks, in response to the selection of the second item being received.

2. The method of claim 1, wherein the specimen is a biological specimen extracted from an examinee.

3. The method of claim 2, wherein in the transmitting the examination result, information about a status of the examinee is transmitted together therewith.

4. The method of claim 1, wherein the result of quality control testing is conducted using quality control serum or an electronic quality control material for quality control of the medical device.

5. The method of claim 4, wherein the result of the quality control testing of the medical device is performed automatically by the medical device for every predetermined period or manually by a user.

6. The method of claim 4, wherein the result of quality control testing of the medical device is determined automatically by the medical device or by the at least one destination.

7. The method of claim 1, wherein the two or more destinations comprise at least one from among a server of a medical institution, a server of a medical information collection organization, and a mobile device held by an individual member of medical staff.

8. The method of claim 7, wherein the server of the medical institution and the server of the medical information collection organization are electronic medical record (EMR) servers.

9. The method of claim 7, wherein at least one from among the server of the medical institution and the server of the medical information collection organization retransmits the examination result to the mobile device held by the individual member of medical staff.

10. The method of claim 1, wherein when the result of quality control testing is transmitted, a predetermined destination is set as default destination information.

11. The method of claim 1, wherein the destination information is received automatically from an emergency management server or input directly to the medical device.

12. The method of claim 1, wherein the destination information comprises at least one from among a Uniform Resource Locator (URL), an Internet Protocol (IP) address, an Email address, and a telephone number of the destination.

13. The method of claim 1, wherein the medical device and the two or more destinations are connected to each other via the networks, and
the networks comprise at least one from among an Internet network, an Email network, a wireless communication network, a Short Message Service (SMS) network, and a Multimedia Messaging Service (MMS) network.

14. A medical device for transmitting an examination result of a specimen to a destination, the medical device comprising:
a specimen inserter configured to insert the specimen;
a wireless communication unit configured to receive destination information indicating two or more destinations to which the examination result is to be transmitted;
a display;
a processor configured to:
examine the specimen to generate the examination result;
process the examination result;
control the display to display the destination information together with priority information for each of the two or more destinations;
determine at least one destination from among the two or more destinations;
control the display to display a transmission setting screen for the determined at least one destination, wherein the transmission setting screen indicates networks usable to transmit the examination result to the determined at least one destination;
receive a selection of at least one of the networks indicated by the displayed transmission setting screen;
receive a selection of at least one from among a first item representing the examination result of the specimen and a second item representing a result of quality control testing of the medical device;
control the wireless communication unit to transmit the examination result of the specimen, to the determined at least one destination, via the selected at least one of the networks, in response to the selection of the first item being received; and
control the wireless communication unit to transmit the result of quality control testing of the medical device, to the determined at least one destination, via the selected at least one of the networks, in response to the selection of the second item being received.

15. The medical device of claim 14, wherein the specimen is a biological specimen extracted from an examinee.

16. The medical device of claim 15, wherein the examination result is transmitted together with information about a status of the examinee.

17. The medical device of claim 14, wherein the specimen is quality control serum or an electronic quality control material for quality control testing of the medical device.

18. The medical device of claim 17, wherein the result of the quality control testing of the medical device is performed automatically by the medical device for every predetermined period or manually by a user.

19. The medical device of claim 17, wherein the result of quality control testing of the medical device is determined automatically by the medical device or by the at least one destination.

20. The medical device of claim 14, wherein the destination information is received automatically from an emergency management server or input directly to the medical device.

21. The medical device of claim 14, wherein a predetermined destination is set as default destination information.

22. The medical device of claim 14, wherein the destination information includes at least one from among a Uniform Resource Locator (URL), an Internet Protocol (IP) address, an Email address, and a telephone number of the destination.

23. The medical device of claim 14, wherein the medical device is connected to the two or more destinations via the networks, and
the networks comprise at least one from among an Internet network, an Email network, a wireless communication network, a Short Message Service (SMS) network, and a Multimedia Messaging Service (MMS) network.

24. A non-transitory computer-readable recording medium having recorded thereon a program for executing a method of transmitting an examination result of a specimen, from a medical device to a destination, the method comprising:
examining the specimen, using the medical device;
receiving, by the medical device, destination information indicating two or more destinations to which the examination result is to be transmitted;

displaying, by the medical device, the destination information together with priority information for each of the two or more destinations;

determining, by the medical device, at least one destination from among the two or more destinations;

displaying, by the medical device, a transmission setting screen for the determined at least one destination, wherein the transmission setting screen indicates networks usable to transmit the examination result to the determined at least one destination;

receiving, by the medical device, a selection of at least one of the networks indicated by the displayed transmission setting screen;

receiving a selection of at least one from among a first item representing the examination result of the specimen and a second item representing a result of quality control testing of the medical device;

transmitting the examination result of the specimen, to the determined at least one destination, via the selected at least one of the networks, in response to the selection of the first item being received; and transmitting the result of quality control testing of the medical device, to the determined at least one destination, via the selected at least one of the networks, in response to the selection of the second item being received.

* * * * *